(12) United States Patent  
Coombs

(10) Patent No.: US 7,936,459 B1
(45) Date of Patent: *May 3, 2011

(54) APPARATUS WITH PROBE

(76) Inventor: David Coombs, Fredericton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/755,616

(22) Filed: Apr. 7, 2010

Related U.S. Application Data

(63) Continuation-in-part of application No. 11/984,764, filed on Nov. 21, 2007, now Pat. No. 7,724,372.

(60) Provisional application No. 60/860,217, filed on Nov. 21, 2006.

(51) Int. Cl.
*G01N 21/00* (2006.01)

(52) U.S. Cl. ........................................ 356/436

(58) Field of Classification Search .......... 356/432–445, 356/72–73, 5.1, 5.01; 600/310, 320, 473, 600/476

See application file for complete search history.

(56) References Cited

U.S. PATENT DOCUMENTS

| | | | |
|---|---|---|---|
| 4,003,834 A | 1/1977 | Coombs | |
| 4,873,875 A | 10/1989 | Cork | |
| 4,940,333 A | 7/1990 | Pawliszyn | |
| 5,645,715 A | 7/1997 | Coombs | |
| 6,014,204 A * | 1/2000 | Prahl et al. | 356/73 |
| 6,023,340 A | 2/2000 | Wu et al. | |
| 6,370,406 B1 * | 4/2002 | Wach et al. | 600/310 |
| 6,479,239 B1 | 11/2002 | Anderson et al. | |
| 6,485,427 B1 | 11/2002 | Lee et al. | |
| 6,526,309 B1 * | 2/2003 | Chance | 600/473 |
| 7,374,540 B2 | 5/2008 | Schnall | |
| 7,724,372 B1 * | 5/2010 | Coombs | 356/436 |
| 2007/0232874 A1 * | 10/2007 | Ince | 600/320 |

* cited by examiner

*Primary Examiner* — Sang Nguyen

(57) ABSTRACT

An apparatus adapted to obtain a profile of a density gradient sample independently of fractionation is provided. The apparatus includes a light source, a probe comprising a first probe needle actuatable to extend into a tube containing a sample, a first light-transmitting means to receive light from the light source and transmit light through the sample as the probe needle extends into the sample, a second light-transmitting means to receive light transmitted by the first light-transmitting means and transmit the received light to a signal-producing means capable of translating the received light into a recordable signal to produce a profile of the sample. The apparatus may additionally be adapted to fractionate the sample following generation of the gradient profile.

8 Claims, 12 Drawing Sheets

A)

B)

A)

B)

A)

B)

APPARATUS WITH PROBE

This application is a continuation-in-part application of U.S. patent application Ser. No. 11/984,764, filed on Nov. 21, 2007, and this application also claims the benefit of U.S. Provisional Application No. 60/860,217, filed on Nov. 21, 2006, the entire contents of which prior applications are hereby incorporated herein by reference.

FIELD OF THE INVENTION

The present invention relates to an apparatus useful to probe a solution gradient. In particular, the present invention relates to an apparatus comprising a probe adapted to generate a gradient profile of a density gradient independent of fractionation.

BACKGROUND OF THE INVENTION

Solution gradients or density gradients are utilized in biochemical research to separate macromolecules such as proteins, DNA and RNA, and larger aggregates such as viruses and cells. More recently, density gradient centrifugation has found application in the field of nanotechnology. Researchers at Northwestern University have used gradients to separate and purify different classes of carbon nanotubes.

Solution gradients usually utilize a solute of varying concentrations to aid in the separation of particles. Examples of appropriate solutes are: sucrose, glycerol, CsCl, Optiprep™, Percoll™, ficoll, metrizamide, Nycodenz.™ and/or sodium acetate. Particles are separated during centrifugation either by their velocity of sedimentation, or by their density if there is an isopycnic point within the solution column in the tube. Faster, or denser particles, respectively, will appear lower in the tube.

After the sample has been subjected into the appropriate density gradient in the centrifuge, the particles are recovered from the gradient for analysis. Fractionation methods and apparatus used to recover the sample in the gradient involve the transfer of the entire gradient or certain layers or bands of the solution gradient to other vessels. It is often desired to extract only desired bands from the solution gradient for electron microscopy, liquid scintillation or gel electrophoresis.

One of the earliest and simplest methods of fractionation is to pierce the bottom of the centrifuge tube with a fine bevelled needle and collect the drops of the solution gradient as it flows through the needle into a second vessel. The flow of the solution into the opening of the needle becomes conical. In other words, the particles directly in front of the needle opening and within a zone best described as an inverted cone above the needle are drawn into the needle opening before particles outside the cone. The resulting fractionation of different layers of the solution gradient significantly degrades the resolution achieved in the gradient.

Bottom puncture with side hole needles have also been used for fractionation. Side hole needles have a hole on each side of the needle tip. Side hole needles are more effective than the bevelled needle, but side hole needles also draw the solution into the needle in a conical fashion preventing high resolution of the fractionation.

One of the most common methods for fractionating solution gradients introduces a dense solution at the bottom of the centrifuge tube, which floats the gradient up to an inverted collection funnel placed on the top of the gradient. Some loss of resolution results from the retardation of particles near the tube wall during this upward movement, and at any but the slowest flow rates, the shallow collection cone fails to prevent the shallow collection cone fails to prevent the same cone-shaped extraction of liquid directly below the cone's central orifice experienced by the bevelled needle described above. The result is mixing of different layers in the gradient and the resultant loss of resolution.

These problems were addressed in U.S. Pat. No. 4,003,834 to Coombs, issued Jan. 18, 1977, an apparatus is disclosed for the fractionation of a solution gradient by displacement with a piston, and in U.S. Pat. No. 5,645,715 to Coombs issued 1995 which discloses a piston collection tip with a unique trumpet shape collection face. The use of a piston to displace the gradient from the top down solves the problem of particles adhering to the wall during the upward movement of the entire gradient since the gradient remains stationary until it is displaced by the downward movement of the piston. The trumpet tip prevents the cone-shaped mixing by gradually compressing horizontal bands into thin vertical columns prior to collection. Tubing carrying both air and rinse is disposed within the piston to allow for cleaning of the collection tubing, further improving resolution by preventing cross contamination between fractions. Pumping air into the piston tip transfers any solution gradient left in the tubing to a second vessel.

U.S. Pat. No. 4,003,834 also provides a means for visualizing bands of particles large enough to scatter visible light. However, many particles of interest are too small to scatter visible light or are present at too low a concentration to be detected. Since the nucleic acids and proteins found in these particles absorb UV light in the 260-280 nm range, it is the current practice to detect bands of these particles by passing the gradient outflow through a UV flow cell as is frequently done in HPLC and FPLC. The UV gradient profile obtained by the flow cell can be used as a diagnostic tool in its own right; however, in this application, the profile is generated as the gradient is being removed from the centrifuge tube.

There are two potential problems with this type of UV-based fractionation. Firstly, it is difficult to accurately and reproducibly identify the beginning and end of UV absorbance peaks (bands) in the profile as it is being generated. Secondly, unless the user manually interrupts the flow at the start and end of each peak, the fraction collector typically used to separate the gradient outflow into discrete fractions is doing so at a constant time interval or rate of flow. Thus, there is no relationship between the peaks of absorbance and the fractions and this requires the user to scan a range of fractions to identify those containing the particles of interest. Some UV-based collection systems have "peak-picking" algorithms built into their software so that rapid changes in UV absorbance in the outflow trigger sample collection into a new vessel. While providing adequate separation of discrete peaks of particles, these devices have difficulty detecting and separating overlapping peaks or shoulders. Volume- or time-based fractionation of the UV-flow cell output is disrupted by peak-picking, so the overall sampling profile is then lost. Thus, one must choose between obtaining uniform size samples for analysis or isolating peaks, as they are mutually exclusive.

Certain inventions (i.e. U.S. Pat. Nos. 4,873,875; 6,479, 239) have attempted to obtain a UV or fluorescent profile of the contents of a centrifuged gradient by vertically scanning the gradient with a beam of light from the outside of the tube. These have not seen widespread use because the only centrifuge tubes that can withstand the severe stress of ultracentrifugation (100,000-1,000,000×g) are made of a UV-absorbing plastic, effectively preventing the beam from penetrating the tube. Consequently, the only devices currently capable of producing a UV profile of a gradient are those which pass the gradient through a detached UV flow cell.

It would be desirable, thus, to develop a means of generating a gradient profile independent of fractionation that may be used as a guide to fractionation.

SUMMARY OF THE INVENTION

An apparatus has now been developed which is useful to obtain a profile of a density gradient. The apparatus comprises a probe adapted to obtain a gradient profile optically. The probe advantageously causes minimal disturbance of the gradient and thereby provides a gradient profile of high resolution.

Thus, in one embodiment, an apparatus is provided adapted to obtain a gradient profile. The apparatus includes a light source, a probe comprising a first probe needle actuatable to extend into a tube containing the gradient, said probe being in communication with the light source and comprising a first light-transmitting means to receive light from the light source and transmit light through the gradient as the probe needle extends into the gradient, and a second light-transmitting means to receive light transmitted by said first light-transmitting means and transmit the received light to a signal-producing means.

In another aspect of the present invention, there is provided a fractionation apparatus adapted to obtain a gradient profile of a density gradient independently of fractionation. The fractionation apparatus comprises:

a light source;

a probe comprising a first probe needle actuatable to extend into a tube containing the gradient, said probe being in communication with the light source and comprising a first light-transmitting means to receive light from the light source and transmit light through the gradient as the probe needle extends into the gradient, and a second light-transmitting means to receive light transmitted by said first light-transmitting means and transmit the received light;

a signal-producing means positioned to receive light from the second light-transmitting means, wherein said signal-producing means translates the received light into a recordable signal to produce a profile of the gradient; and a piston actuatable to extend into the gradient-containing tube and to fractionate the gradient according to the sample profile;

wherein the probe and piston are moveable between a resting position wherein the probe and piston are clear of the gradient tube, a probing position wherein the probe is in a gradient access position and a fractionating position wherein the piston is in a gradient access position, said probe and piston being independently actuatable.

In another aspect of the present invention, a method of fractionating a gradient is provided comprising:

i) determining the profile of a gradient;

ii) selecting a fractionation plan according to the profile; and iii) executing fractionation of the gradient according to the plan.

In a further aspect of the invention an apparatus adapted to obtain a profile of a stationary density gradient sample using fluorescence is provided. The apparatus comprises:

a light source;

a probe comprising a first probe needle actuatable to extend into a tube containing the gradient, said probe being in communication with the light source and comprising a first light-transmitting means to receive light from the light source and transmit light having an excitation wavelength into the gradient as the probe needle extends into the gradient, and a second light-transmitting means to transmit received light to a signal-producing means, wherein the first light transmitting means comprises a transmitting fibre optic bundle and a first reflection means and the second light-transmitting means comprises a second reflection means and a receiving fibre optic bundle, said light being transmitted by the transmitting fibre optic bundle and reflected by the first reflection means into the gradient at an angle of about 90° to the first probe needle, wherein the light strikes particles in the gradient and causes the particles to emit light at an emission wavelength which is received by said second light-transmitting means and is reflected by said second reflection means to said receiving fibre optic bundle and transmitted by said receiving fibre optic bundle to a signal-producing means; and a signal-producing means adapted to receive light from the second light-transmitting means, said signal-producing means comprising a photodetector to translate the light into a recordable signal to produce a profile of the gradient.

These and other aspects of the present invention will become apparent by reference to the detailed description, and the drawings in which:

DETAILED DESCRIPTION OF THE INVENTION

Figure 1:
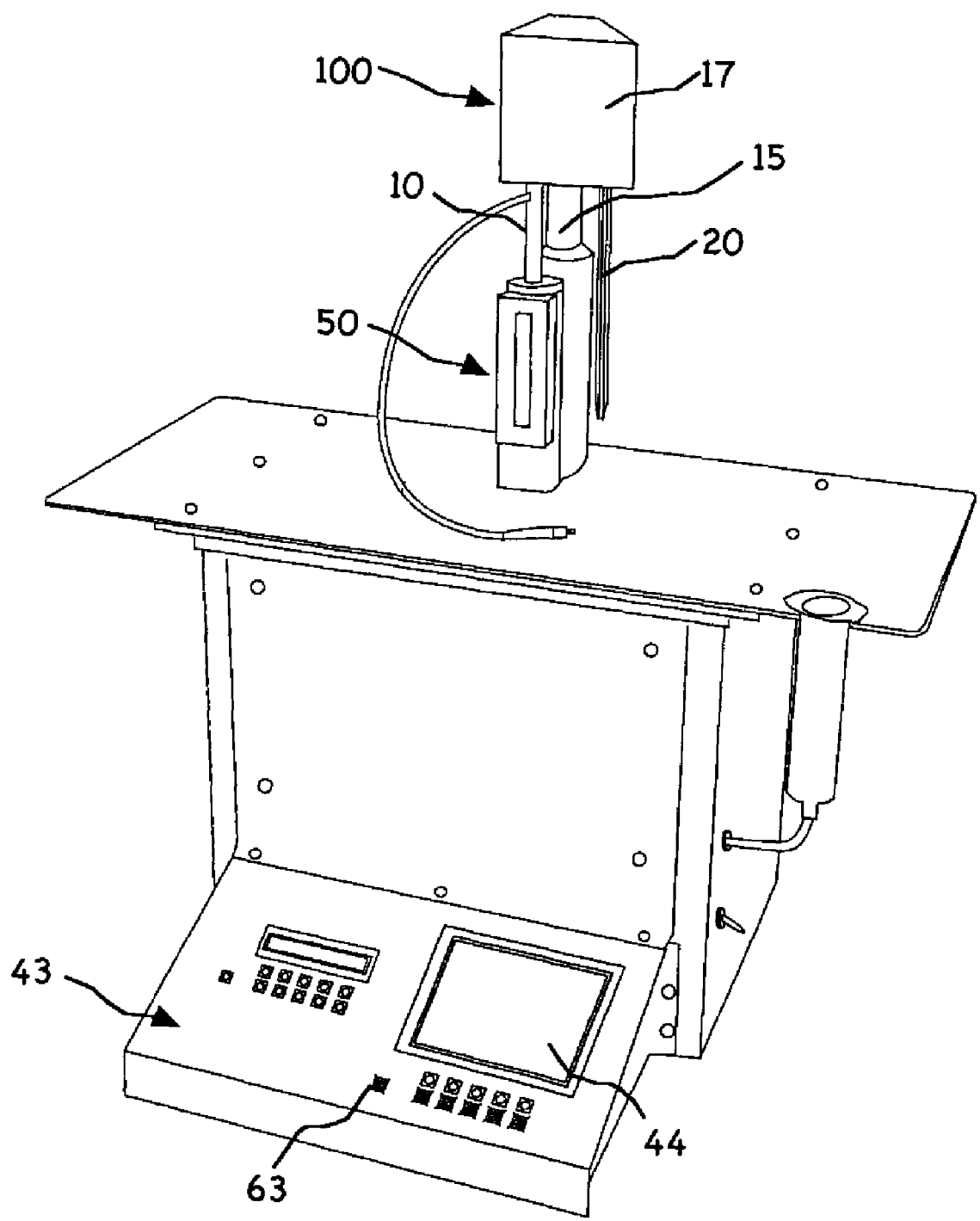
FIG. 1 is a perspective view of an apparatus according to an aspect of the invention.
Figure 2:
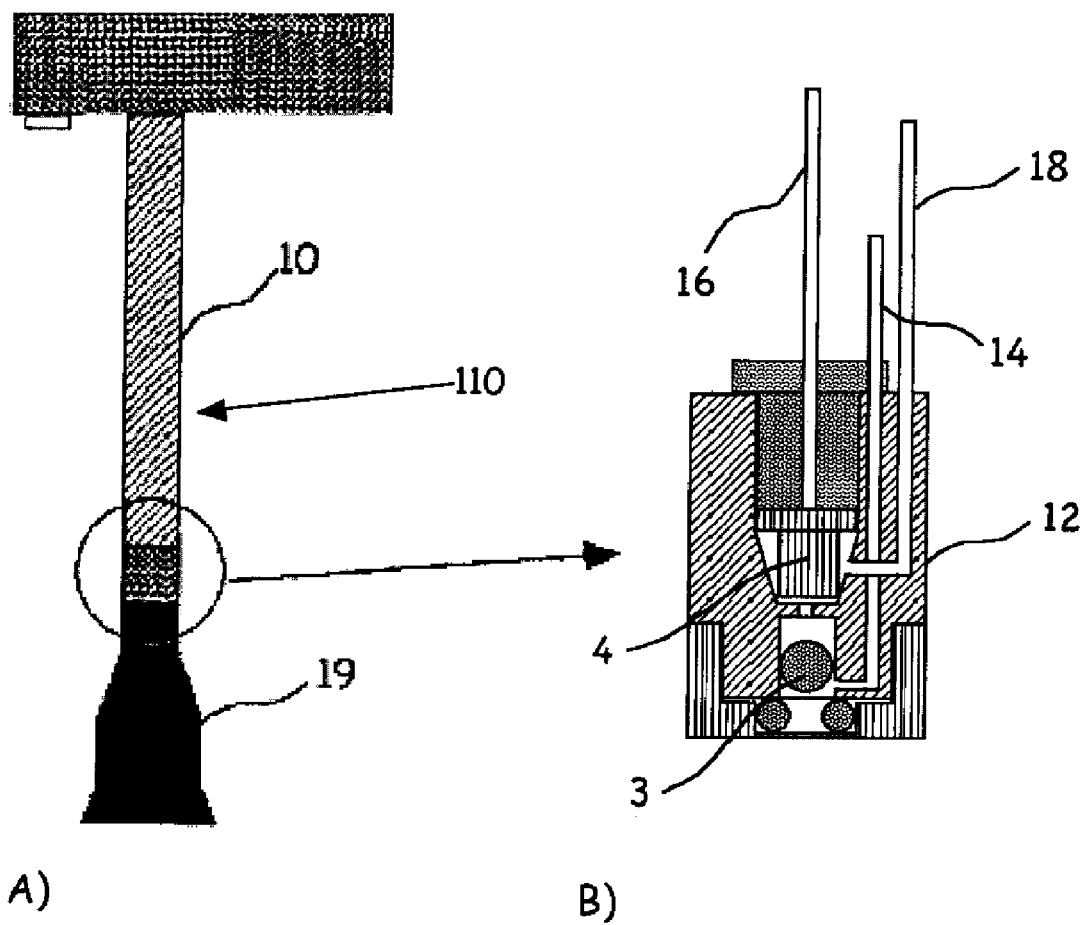
FIG. 2 is a side view of the fractionation portion of an apparatus of FIG. 1 and an exploded view (A) of the valves therein.

A fractionation apparatus 100 is provided as shown in FIG. 1 comprising a fractionation or collection portion 110 and a probe portion 120 useful to generate a profile of a density gradient that can be converted into a fractionation run. The fractionation portion 110 of the apparatus 100 generally corresponds with that described in U.S. Pat. No. 5,645,715, the relevant portion of which (found in columns 3-7) is incorporated herein by reference. As described, and as generally shown in FIG. 2, the fractionation portion 110 comprises a piston 10 having an internal passageway or valve 12, and inserted within the valve 12 are a collection tube 14, an air tube 16 and a rinse tube 18. Mounted below the valve 12 on the end of the piston 10 is a collection tip 19, which may optionally be an interchangeable collection tip as described in U.S. Pat. No. 5,645,715.

As one of skill in the art will appreciate, the configuration described in U.S. Pat. No. 5,645,715 may be modified as shown in FIG. 2 (A) to increase efficiency. For example, the valve 12 may incorporate two one-way valves to permit the rinsing and drying of the sample tubing without disturbing the gradient. The first one-way valve is a ball valve 3 which prevents backflow of air or rinse into the gradient, while the second one-way valve is a rubber duckbill 4 valve which prevents backflow of rinse and gradient into the air tubing. Backflow of air and gradient into the rinse line is prevented by a rubber duckbill one-way valve mounted in the tubing between the rinse pump and the piston.

Figure 3:
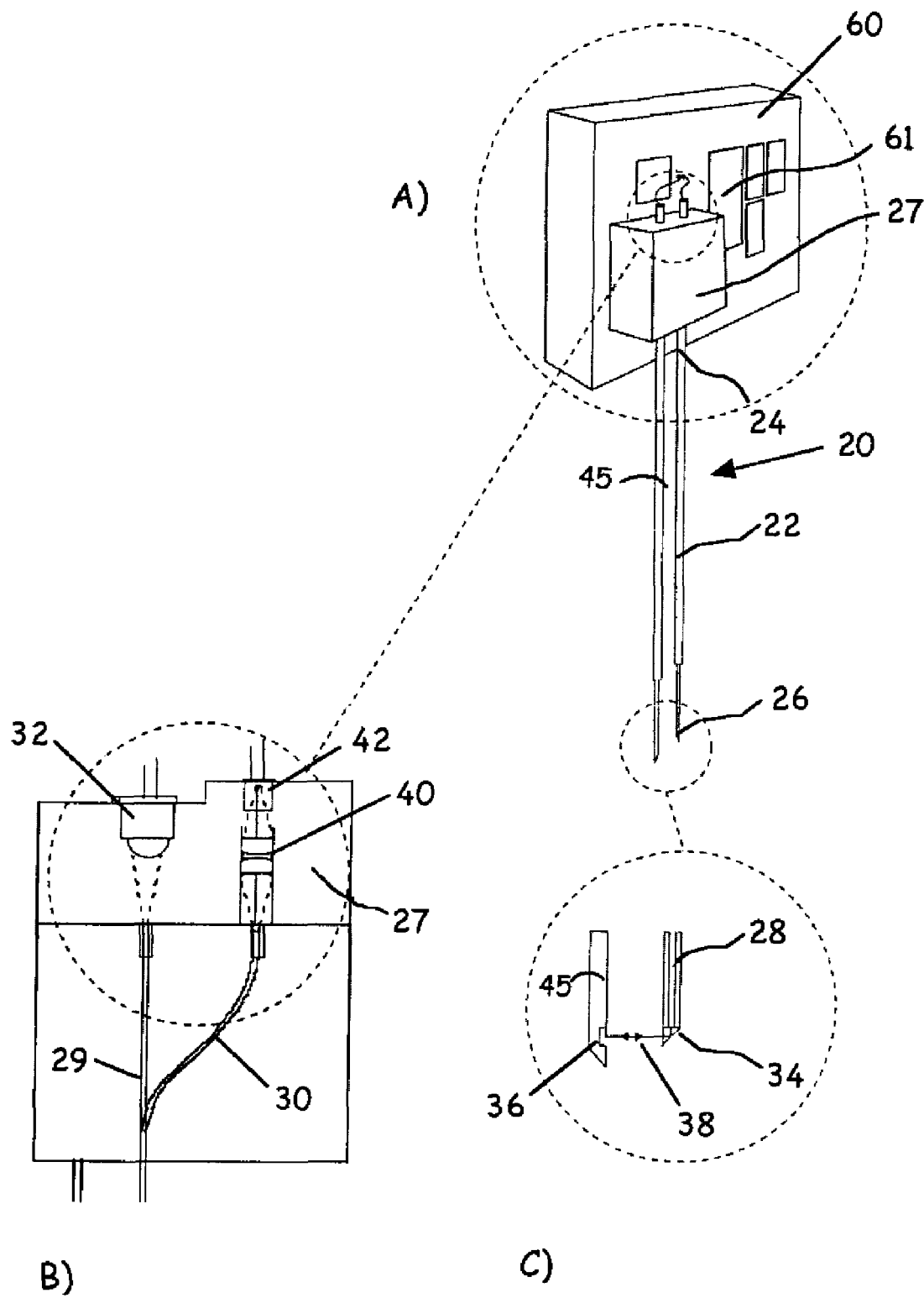
FIG. 3 is a perspective view of the probe portion of an apparatus of FIG. 1 and exploded views of the tip of the probe needle (A) and light source/photodetector (B)
Figure 4:
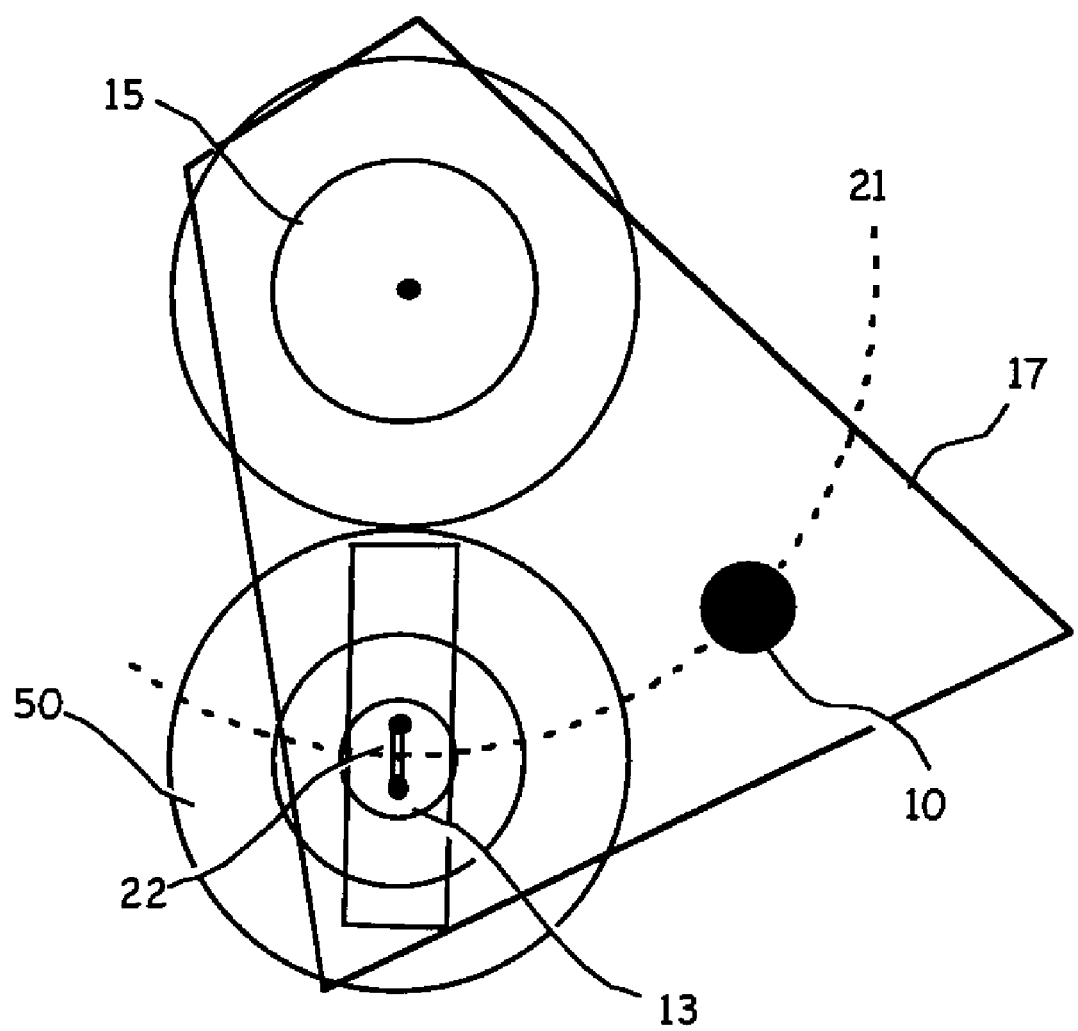
FIG. 4 is a top view illustrating the arc of movement of a probe, piston and actuator of an apparatus of FIG. 1.
Figure 5:
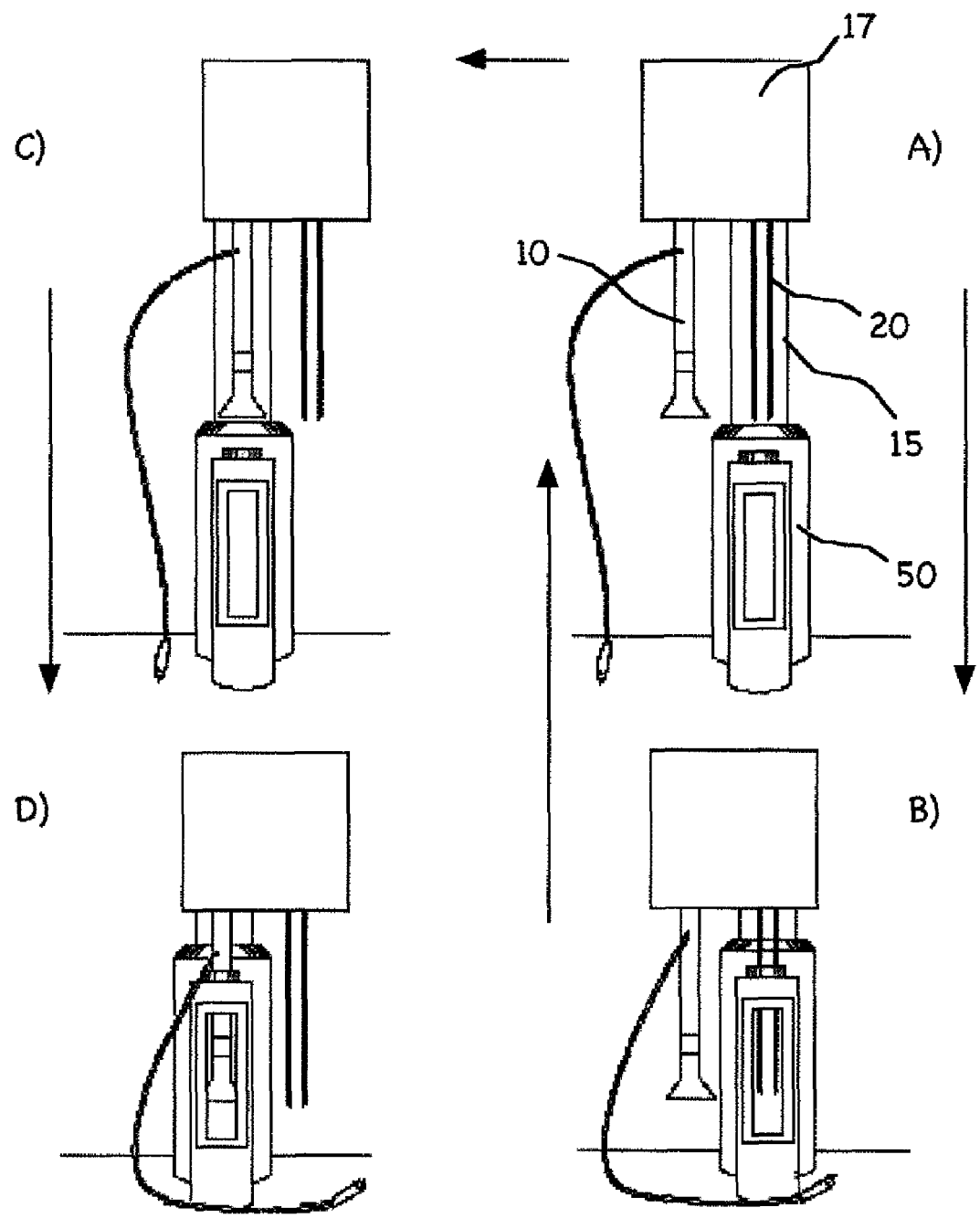
FIG. 5 illustrates the first probing position (A/B) and second fractionating position (C/D) of the apparatus of FIG. 1.

Referring to FIGS. 1 and 3, the fractionation apparatus 100 of an embodiment of the invention comprises a probe portion 120 situated adjacent to the piston 10. The probe portion 120 comprises a probe 20. The probe 20 consists of at least one hollow probe needle 22 which is open at both ends. The probe needle 22 has an upper end 24, which is secured to a mounting block 27, and a lower end 26. The probe 20 and piston 10 are both mounted on a platform or swing arm 17. The swing arm 17 is mounted onto an actuator 15. As shown in FIG. 4, the center of the piston 10 and the center of the probe needle(s) 22 are positioned on the same radial arc 21. The arc is centered on the actuator 15 such that rotation of the actuator 15 positions either the probe 20 or the piston 10 over the gradient tube holder 50 (FIG. 1) of the apparatus 100. Thus, as shown in FIG. 5, the swing arm 17 and actuator 15 are moveable between a fully retracted resting position in which both the piston 10 and probe 20 are clear of a tube holder 50 which holds the gradient, a first or probe position in which the probe 20 is in position centered above tube holder 50 (FIG. 5(A)) and a second or fractionating position in which the piston 10 is positioned centered above the tube holder 50 (FIG. 5(C)).

Figure 9:
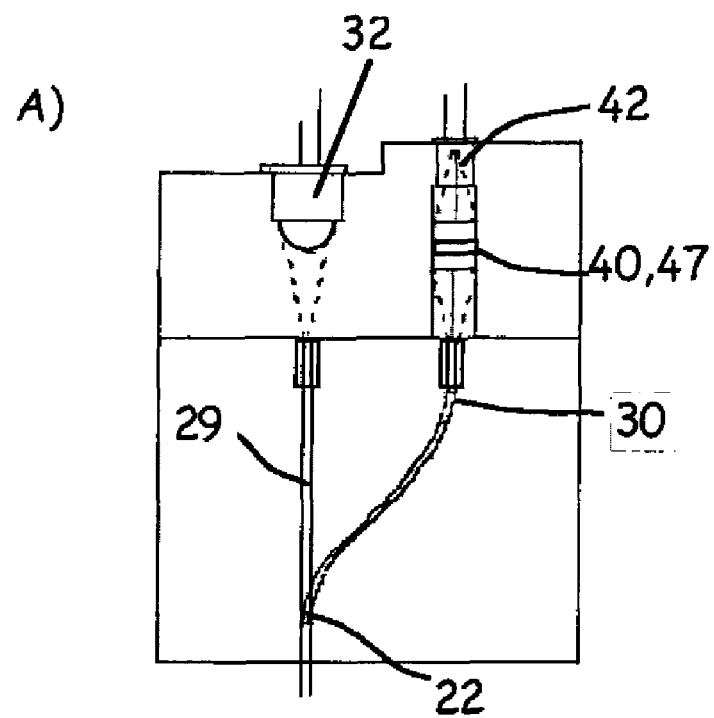
FIG. 9 illustrates an embodiment of the invention
Figure 9:
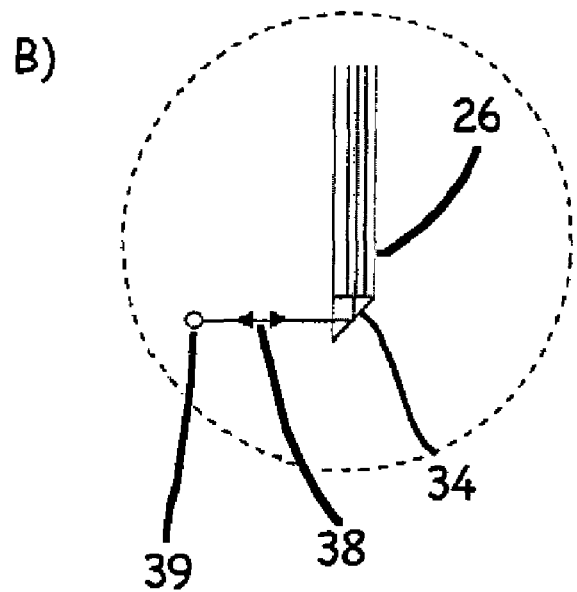

The actuator 15 also functions to lower each of the probe 20 and piston 10, respectively, when in position above the tube holder 50, into a sample gradient tube 13 as illustrated in FIG. 9. The actuator 15 may be manual, as illustrated and described in U.S. Pat. No. 4,003,834, the relevant disclosure of which (e.g. columns 3-7) is incorporated herein by reference. Alternatively, the apparatus may be fully automated by incorporating a computer to drive a stepper motor to rotate an acme screw which raises and lowers the actuator 15, providing means for precisely determining the position and velocity of both the piston 10 and the probe 20. This ensures that the extension of the probe 20 into the sample is conducted at a constant velocity such that each data point in the UV profile is coupled with its precise position in the gradient.

Figure 6:
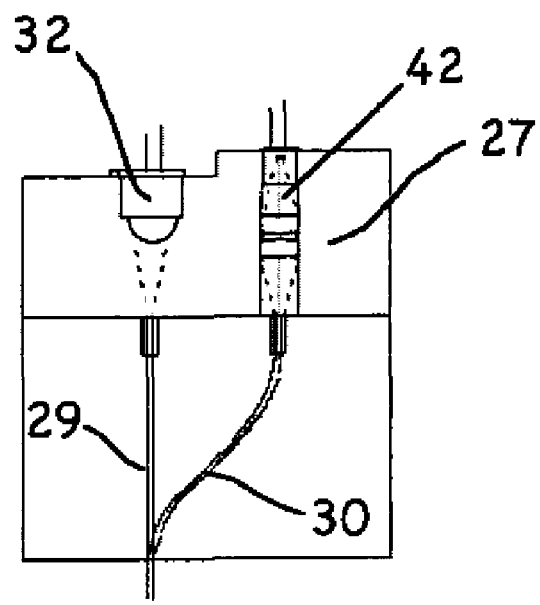
FIG. 6 illustrates an embodiment of the invention.
Figure 6:
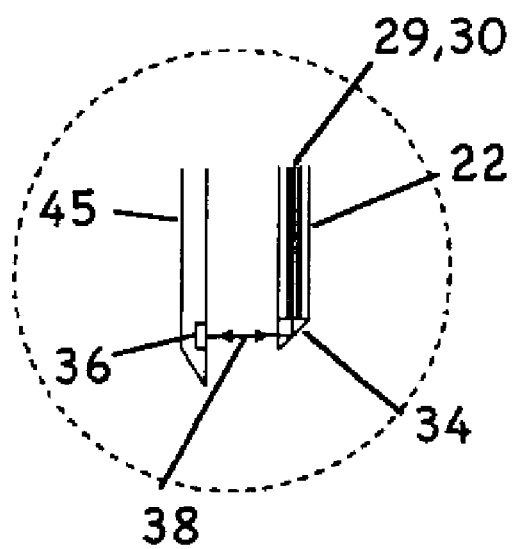

The probe needle 22 contains fiber optic bundles 28. In one embodiment, as illustrated in FIG. 6, the fibre optic bundles 28 within the probe needle 22 include a mixed and randomized fibre optic transmitting bundle 29 and a fibre optic receiving bundle 30 (FIG. 6B), each of which extend the length of the probe needle 22. The transmitting bundle 29 is connected to a suitable light source 32, such as an LED emitting in a selected wavelength range. For detection of UV-absorbing particles, the transmitting bundle 29 connects to a suitable UV source such as an ultra-violet light emitting diode (UV LED). In alternative embodiments, the light source may be an LED emitting in the visible range. The light source 32 is mounted onto the mounting block 27. A photodetector 42 is also mounted on the mounted block 27 approximately adjacent to the light source 32 (FIG. 6A).

As one of skill in the art will appreciate, each fibre optic bundle will incorporate fibres manufactured of material appropriate for the transmission of the wavelength of the light emitted from the light source 32. For example, if the light source 32 emits in the UV range from 250 to 350 nm, quartz (fused silica) fibres may be used. The number and diameter of the fibres in the fibre optic bundle is optimized empirically to provide the highest signal to noise ratio and the highest resolution in a given application. For example, in certain embodiments, such as those illustrated in FIGS. 6-9, 80 fibres with 0.1 mm diameter are utilized. In these embodiments, the choice of 80 fibres was based on the fact that fewer fibres produce a weaker signal while more fibres require a larger diameter needle and result in greater disturbance during the probing of the gradient. In certain embodiments, such as those illustrated in FIGS. 6, 8 and 9, the fibres are split into two independent bundles, a transmitting bundle 29 and a receiving bundle 30.

A reflection means 34 is permanently attached to the bottom end 26 of the probe needle 22 which functions to reflect a beam of light received from the light source 32, conducted the length of the probe needle 22 by the transmitting bundle 29, into the gradient. The reflecting means 34 reflects the light beam into the gradient towards a second reflection means 36, for example, at a 90° angle to the probe needle 22. The reflected beam exits the needle 22, travels a gap 38 through the gradient and is then deflected by the second reflection means 36 back along the same plane towards the first reflection means 34, e.g. at an angle of 180°. The gap 38 between the first and second reflection means 34, 36 is sufficient to render a suitably accurate reading of the gradient. The first and second reflection means 34, 36 may be any means capable of reflecting the light beam at the required angle. In this embodiment, for example, a prism is appropriate for use as the first reflection means 34 having a 45° reflecting angle. While many sizes of prism will be suitable, the prism exemplified in one embodiment has cross section dimensions of: 1.0 mm.×1.0 mm. on both 90° faces and 1.4 mm along the hypotenuse reflector surface. The length of the prism matches the length of the end of the needle, e.g. 2.9 mm.

The second reflection means 36 is affixed to a support 45 sufficient to position it appropriately from the probe needle 22. The support 45 may be a support needle (as shown in FIG. 3) generally aligned parallel to the probe needle 22 such that it is appropriately spaced from the needle 22 to provide gap 38. Generally, the gap 38 between the first and second reflection means 34, 36 is in the range of 1-10 mm. Since an increase in gap size will result in increased absorbance, and a decrease in gap size will result in a stronger signal, the gap 38 between the first and second reflection means 34, 36 may be adjusted in order to maximize resolution in view of the variability among gradients. The support needle 45 containing the reflecting means 36 is shown mounted onto mounting block 27 such that it will co-extend into the gradient simultaneously with the probe needle 22 on actuation of actuator 15.

The second reflecting means 36 comprises a 180° reflecting angle and may be, for example, a planar mirror. Its minimum dimensions are the dimensions of the beam it is to reflect, for example, 0.3×2.6 mm, but may, of course be larger to reduce the stringency of its positioning on the support needle 45. As indicated above, the second reflection means 36 is positioned to reflect the incident beam from the probe needle 22 back and into the receiving fibres 30 within the end of the probe needle 22.

Figure 10:
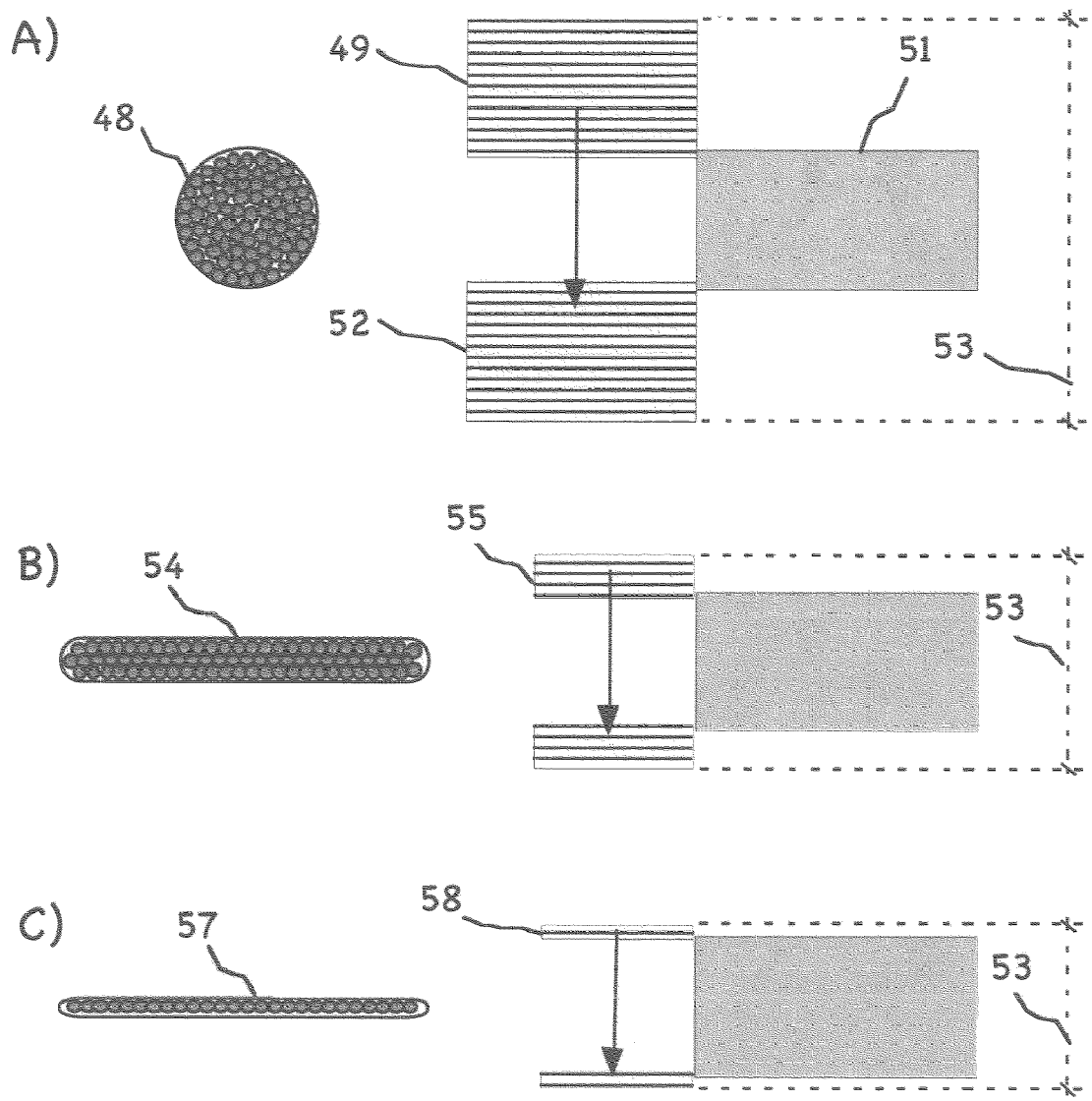
FIG. 10 illustrates different geometries of the probe needle tip.

As shown in FIG. 10, the geometry of the probe needle end 26 has a significant impact on the resolving power of the probe needle 22. In one example, the transmitting/receiving fibre bundle 29, 30 may be circular 48 (FIG. 10A) at the bottom end 26 of the probe needle 22, producing a cylindrical beam of light 49 that is reflected by the first reflecting means 34 across the gap 38 to the second reflecting means 36. The band of particles in the gradient 51 will first be detected when the bottom edge of the cylindrical beam 49 first encounters the band 51. The band will be detected until the top edge of the beam 52 leaves the band, giving a total distance of detection 53. If the probe needle 22 is flattened at its lower end 26 to a rectangular shape 54 (FIG. 10B), the light beam 55 crossing the gap 38 is much thinner, resulting in a smaller total distance of detection 56 and increased resolution. The dimensions of the rectangle are constrained by the number, diameter and arrangement of the fibers in the bundle. For example, using a bundle of 80 fibers generates a beam having 0.3×2.9 mm rectangular shape. If a single row of fibers is used in a flattened needle 57 (FIG. 10C), the thinnest beam of light 58 is produced and (theoretically) the smallest total distance of detection 59. However, the amount of light available for detection is also much reduced (30% of the two other versions shown since the number of fibres is decreased), so the signal to noise ratio suffers. If the number of fibres remains the same as in the circular and rectangular examples (FIG. 10A/B) (48 and 54), the end of the needle shown in FIG. 10C would be 8 mm across, giving a greater wetted surface area and producing more disturbance of the gradient during insertion and withdrawal of the probe. Thus, the dimensions of the end of the probe needle impact on both resolution and gradient disturbance, and require selection in order to provide an appropriate balance. Dimensions of 0.3 mm×2.9 mm represent an example of a suitable compromise between resolution and disturbance. While bands of particles in a gradient are occasionally 1 mm thick, most bands lie in the 2-5 mm range of thickness, so the 0.3 mm thickness produces a tolerable loss of resolution.

The required electronic circuitry 60 to send and receive the light signal is attached directly to the mounting block 27 (as shown in FIG. 3A) to minimize the sensitivity of the photoreceptor to spurious electronic interference and vibration.

The light beam received and conducted by the receiving fibres 30 is transmitted for detection by a photodetector 42 as shown in FIG. 3. One suitable photodetector for UV light is a 1 mm$^2$ SiC chip contained in a small can with a quartz window (JEC 1S, Boston Electronics, Boston, Mass.). Since the end of the receiving bundle 30 cannot be physically coupled to this chip, and since the light beam diverges at an angle of, for e.g., 17° after it leaves the upper end of the receiving bundle 30 the light beam is transmitted onto a set of condensor lenses 40 which collect and refocus the beam onto the SiC chip inside the can. An example of a suitable set of lenses consists of two plano convex lenses (01LQF005, f=10.0 mm, dia=5 mm, Melles Griot, Ontario, Canada) arranged as shown in the exploded view FIG. 3B.

The photodetector 42 translates the light beam into a recordable output such as current or voltage which is then digitized by a microprocessor 61 such as a Burr Brown microprocessor (DDC-112) and displayed on a display unit 44, such as a monitor, which is connected to the control panel 43 (FIG. 1). The absorbance values collected at regular user-determined intervals, for example, 10 data points/mm, are stored as a spreadsheet associated with the depth in the gradient from which they are taken. The display unit 44 functions in real-time to display the gradient UV absorbance profile throughout the depth of the gradient.

Using the real-time profile, the fractionation is planned by dividing the profile into fractionation zones and by further dividing each zone into a desired number of fractions. This can be accomplished using, for example, a rotary encoder with push switch 63 to move a vertical line cursor across the displayed profile, pressing it down to set the position of the various zones. To synchronize the probing and fractionation functions, both stages of analysis begin with the actuator 15 in its full up resting position where it contacts a limit switch. For each different size tube, for example Beckman's SW28, SW28.1, SW40, SW41, SW55, SW60 and TLS55, the precise vertical offset between the tip of the probe and the point of gradient capture inside the piston tip is determined empirically and stored in memory. Thus, the position of the cursor on the display can be precisely translated into a corresponding piston position during fractionation. Likewise, the position of each zone and the sub-fractions within each zone can readily be calculated. Once the plan has been set on the display, the computer converts the fractionation plan into a series of downward movements of the piston interrupted by a user-selected rinse protocol at the end of each fraction. The speed of the piston's movements is set automatically, but is user-adjustable, with 0.3 mm/sec being a typical speed.

In practice, a gradient profile is obtained using an apparatus according to an aspect of the invention by placing a gradient-containing tube 13 into the tube holder 50. As shown in FIG. 5, the probe 20 is swung into position above the tube and actuated to probe the sample. The probe and support needles (22, 45) are simultaneously lowered into the gradient at a constant speed within the range of 0.1-6.0 mm/sec. As the needles extend into the gradient, light transmitted from the light source 32 is captured by the transmitting fibre optic bundle 29 and is conducted the length of the probe needle 22 to the bottom end 26 thereof where it is reflected at a 90° angle off of the first reflecting means 34. The reflected light travels the gap 38 through the gradient and is reflected at a 180° angle off of the second reflecting means 36. The reflected light re-travels the gap 38, is reflected 90° by the first reflecting means 34, is captured by the receiving fibre optic bundle 30 and is conducted the length of the probe needle 22 to the top end 24 thereof. The returning beam leaves the end of the receiving bundle and is captured by a set of condensor lenses 40 which refocus it for detection by the photodetector 42. The photodetector 42 translates the light received into recordable output that may be displayed graphically, numerically or otherwise on a display unit 44. Upon reaching the bottom of the sample tube, the needles are withdrawn automatically.

Figure 11:
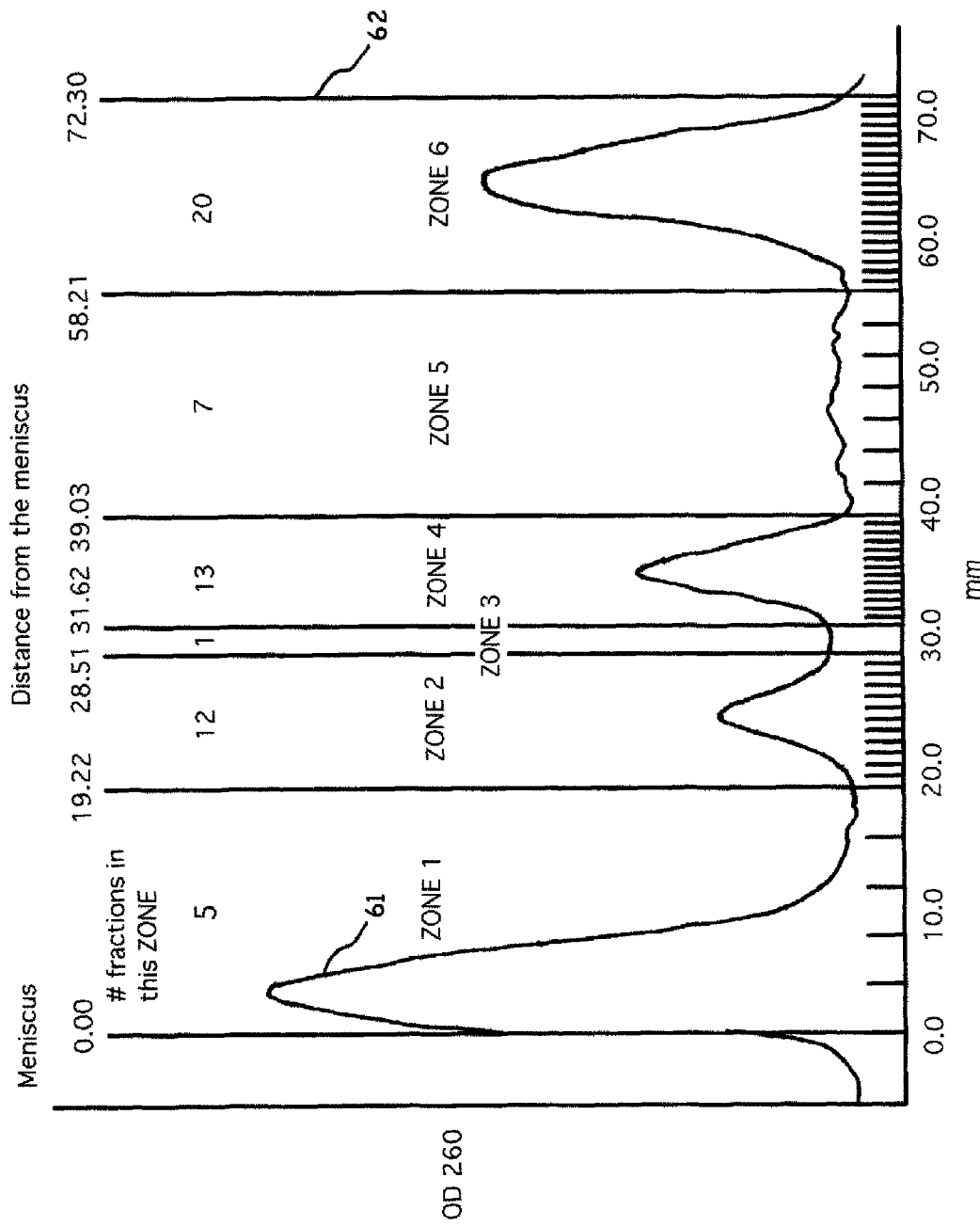
FIG. 11 illustrates the output signal including zone marking of an apparatus of FIG. 1.

The planning stage involves using a combined rotary encoder+push switch 63 connected to the display unit 44, for example, as is a standard feature of any oscilloscope, to move a vertical line cursor along the X-axis of the displayed gradient profile to set the various zones for fractionation. As the user sets each new zone along the profile, the user is prompted to set the number of fractions within that zone as illustrated in FIG. 11. For example, the gradient may be a single zone divided into a number of equal fractions. Alternatively, the gradient may be divided into several zones with a variable number of fractions per zone. This latter mode permits the isolation of individual bands of particles in the gradient for further analysis.

Once the fractionation zones and fractions are selected, the piston 10 is swung into position over the gradient tube and the gradient is then fractionated automatically. The fractionation plan developed by the user in the previous stage is converted by the computer into a series of downward movements of the actuator 15 and piston 10, interrupted by the insertion of brief bursts of rinses and air to expel sample left in the tubing and remove any cross contamination between fractions.

This profiling function of the probe 20 of the present apparatus 100 advantageously provides a means to view the sample gradient and particles of interest therein, and thus, a means to plan the fractionation of the gradient prior to the actual fractionation.

To this point, an embodiment is described in which the apparatus 100 comprises a dual needle probe (22, 45) with one needle (22) containing both the sending and receiving light bundles (29, 30) and the other support needle (45) having mounted thereon a second reflecting means (36) to deflect the beam reflected by the first reflecting means (34) from the transmitting bundle (29) back to the receiving bundle (30), thus effectively doubling the path length of the probe.

Figure 7:
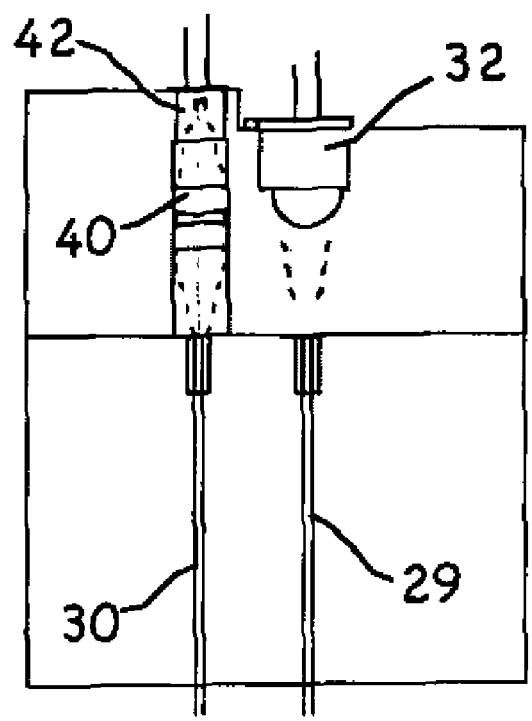
FIG. 7 illustrates an embodiment of the invention.
Figure 7:
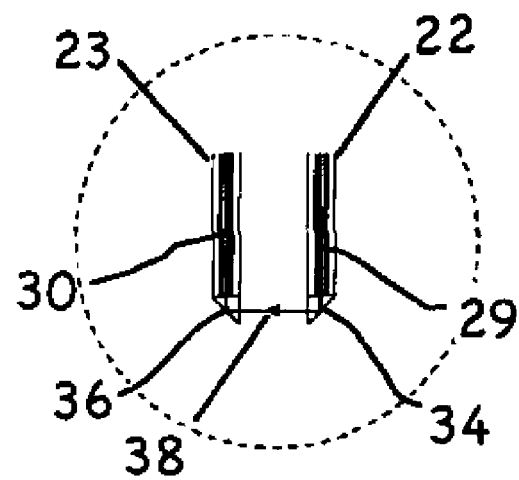

In another embodiment of the present invention, as shown in FIG. 7, the probe 20 includes dual probe needles, a first transmitting probe needle 22 containing a transmitting fibre optic bundle 29 and a second receiving probe needle 23 containing a receiving fibre optic bundle 30. Both bundles will contain an appropriate number of fibers to permit a maximum beam strength and sensitivity, for example, 80 fibres each. As set out above, the first and second probe needles are spaced by an adjustable gap 38 as shown in FIG. 7B. In this case, the first reflecting means 34 is attached to the bottom of the first probe needle 22 such that the light beam passing through the first probe needle 22 is reflected at a 90° angle through the gradient across gap 38. The reflected light beam is received by the second reflecting means 36 which is attached to the bottom of the receiving probe needle 23 such that it reflects the incoming light beam at an angle of 90° to be received by the receiving fibre optic bundle 30 in the receiving probe needle 23. As described, the receiving fibre optic bundle 30 carries the light beam to the top end of the second probe needle 23 where it is transmitted onto a set of lenses 40 for refocusing and then translation by a photodetector 42 to an output signal that forms the profile of the gradient (FIG. 7A). The fractionation plan and fractionation are then executed as described.

Figure 8:
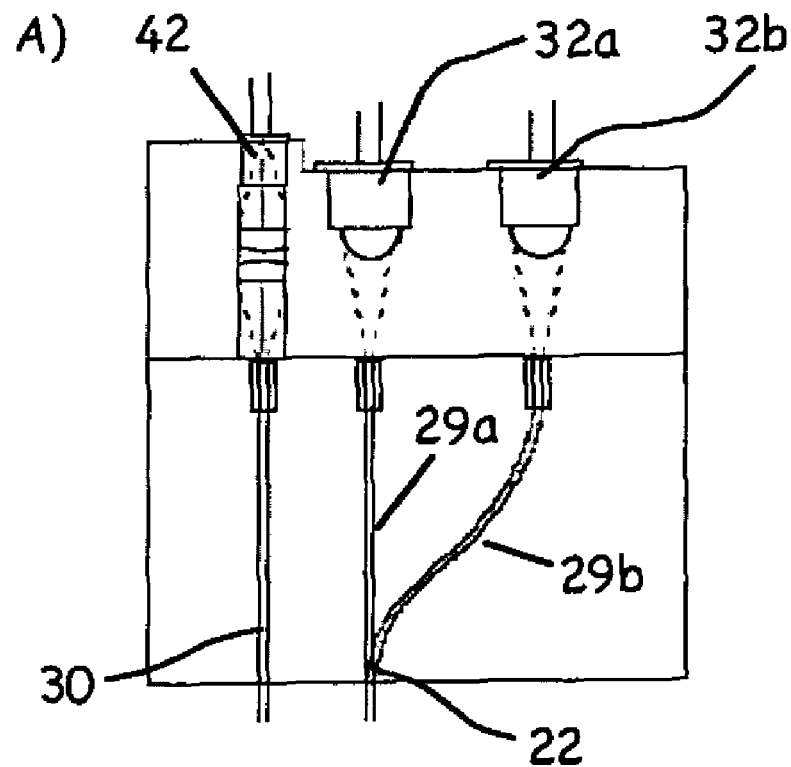
FIG. 8 illustrates an embodiment of the invention.
Figure 8:
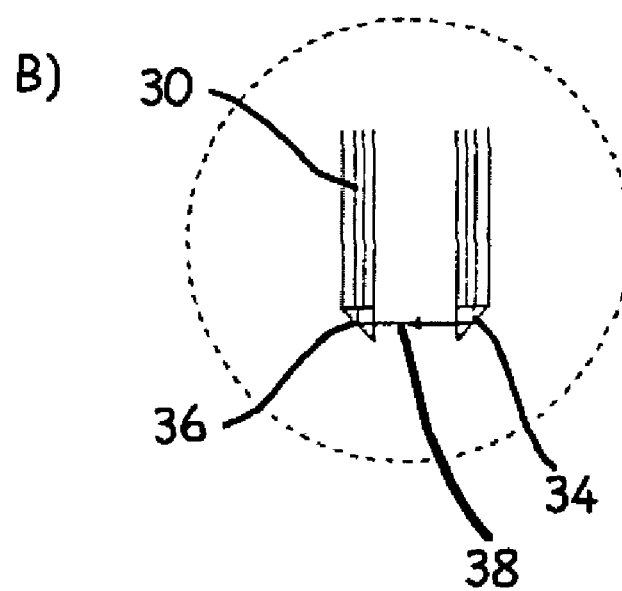

FIG. 8 illustrates another embodiment of the present invention, in which the apparatus 100 incorporates a dual wavelength probe. In this embodiment, the first transmitting probe needle 22 contains two fiber bundles of 40 fibers each. A first wavelength fibre bundle 29a is in communication with a first LED light source 32a that generates light at a first wavelength and a second wavelength fibre bundle 29b is in communication with a second LED light source 32b that generates light at a second wavelength (FIG. 8A). For example, in the case of UV light, the first light source may generate UV light at a wavelength of 260 nm for detection of nucleic acids, while the second light source may generate UV light at a wavelength of 280 nm for detection of proteins. The second receiving probe needle 23 contains a single receiving fibre optic bundle 30 of 80 fibers. In this embodiment, the first and second light sources 32a, 32b transmit light in alternating pulses, which are absorbed by the appropriate transmitting bundle, reflected by the first reflecting means 34 to the second reflecting means 36, reflected by the second reflecting means 36, received and transmitted by the receiving fibre optic bundle 30 in the second receiving probe needle 23. The light received by the photodetector 42 at the top of the receiving needle 23 is sorted by wavelength into two data streams by the microprocessor 61 (e.g. Burr-Brown processor DDC-112), one for each wavelength, generating a dual wavelength profile at the output stage. The fractionation plan and fractionation are then executed as described.

A further embodiment of the present invention is illustrated in FIG. 9. This embodiment comprises a single needle, dual bundle probe; however, rather than measuring the amount of light absorbed by particles in the gradient, this probe is designed to detect particles within the gradient or sample by fluorescence. In this embodiment, the single probe needle 22 houses both transmitting and receiving fibre optic bundles 29, 30 consisting of, for example, 40 fibers each (FIG. 9A). The light source 32 transmits an excitation beam which is carried by the transmitting fibre optic bundle 29 and reflected into the gradient by the first reflecting means 34, e.g. a prism with an appropriate reflecting angle (such as 45°), attached at the bottom of the probe needle 22 as previously described. Particles of interest 39 within the solution, such as microbes or proteins, are detected when they absorb light from the excitation beam having a desired excitation wavelength and then emit light at a different wavelength, e.g. an emission wavelength. The light emitted by the particles 39 strikes the reflecting means 34, is reflected therefrom for receipt by the receiving fibre optic bundle 30 and transmitted to the photodetector 42 for translation as an output signal (FIG. 9B). A filtering means, such as a narrow bandpass filter, 47, placed between the two condensor lenses 40 in front of the photodetector 42 will block light of the excitation wavelength from reaching the photodetector 42, allowing only light of the emission wavelength to pass, as is standard practice in any commercial fluorometer. This configuration can detect particles by their natural fluorescence, by the enhanced fluorescence of a wide variety of commercial dyes that bind specifically to biological molecules of interest or by fluorescent dye-tagged antibodies. For example, viruses can be detected using a DNA-binding dye called PicoGreen (Molecular Probes, Invitrogen, USA) (for example, see "Quantitation of Adenovirus DNA and Virus Particles with the PicoGreen Fluorescent Dye, Murakami P.; McCaman M. T. Analytical Biochemistry, Volume 274, Number 2, October 1999, pp. 283-288"). The excitation light source for PicoGreen delivered by the transmitting bundle 29 is at 485 nm and the emission wavelength received by the receiving bundle 30 in the same probe needle 22 is 538 or 518 nm. These dyes offer sensitivity that is reportedly 10,000 times more sensitive than UV absorbance. Using these dyes converts this absorbance device into a fluorometer probe. A new series of fluorescent dyes (CF™ dyes from Biotium, USA, <www.biotium.com>) have been coupled to antibodies for ultrasensitive detection of target proteins in larger macromolecular assemblies and cells.

As one of skill in the art will appreciate, the embodiment of FIG. 9 may alternatively comprise separate needles (similar to the embodiment shown in FIG. 7), a first needle 22 housing the transmitting bundle 29 and a second needle 23 housing the receiving bundle 30. In this embodiment, the light source 32 transmits an excitation beam which is carried by the transmitting fibre optic bundle 29 and reflected into the gradient by the first reflecting means 34 attached at the bottom of the probe needle 22 as previously described. Particles of interest 39 within the solution absorb light from the excitation beam having an excitation wavelength and then emit light at a different wavelength, e.g. an emission wavelength. The light emitted by the particles 39 strikes the second reflecting means 36, e.g. a prism with an appropriate reflecting angle (such as 45°), attached at the bottom of the second needle 23, is reflected therefrom for receipt by the receiving fibre optic bundle 30 and transmitted to the photodetector 42 for translation as an output signal.

Figure 12:
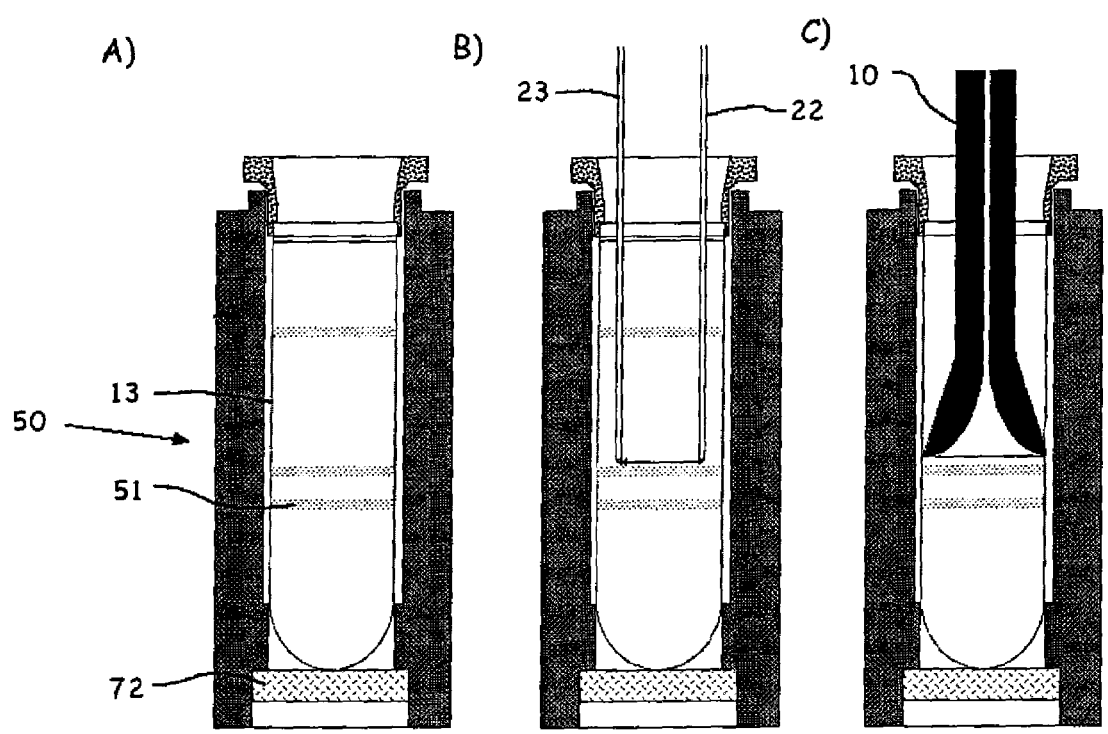
FIG. 12 illustrates the probe (B) and piston (C) of an embodiment of the invention extended within a sample tube.

As will be appreciated by one of skill in the art, the present apparatus 100 may be modified to solely incorporate a probe portion 120 without a fractionation portion 110 as partially shown in FIG. 12B. Such a probing apparatus comprises the features detailed in the foregoing for the probing function of the apparatus and lacks those features necessary to conduct fractionation. Thus, in instances where the desired end product of a gradient-based analyses is the absorbance profile, an apparatus incorporating only a probe portion as described herein may be used.

Although the disclosure describes and illustrates the preferred embodiments of the invention, it is understood that the invention is not limited to these particular embodiments. Many variations and modifications will occur to those skilled in the art. For definition of the invention, reference is made to the appended claims.

References referred to herein are incorporated by reference.

I claim:

1. An apparatus adapted to obtain a profile of a stationary density gradient sample, the apparatus comprising:

a fluorescent light source;

a probe comprising a first probe needle actuatable to extend into a tube containing the gradient, said probe being in communication with the light source and comprising a first light-transmitting means to receive light from the light source and transmit light having an excitation wavelength into the gradient as the probe needle extends into the gradient, and a second light-transmitting means to transmit received light to a signal-producing means, wherein the first light transmitting means comprises a transmitting fibre optic bundle and a first reflection means and the second light-transmitting means comprises a second reflection means and a receiving fibre optic bundle, said light being transmitted by the transmitting fibre optic bundle and reflected by the first reflection means into the gradient at an angle of about 90° to the first probe needle, wherein the light strikes particles in the gradient and causes the particles to emit light at an emission wavelength which is received by said second light-transmitting means and is reflected by said second reflection means to said receiving fibre optic bundle and transmitted by said receiving fibre optic bundle to a signal-producing means; and a signal-producing means adapted to receive light from the second light-transmitting means, said signal-producing means comprising a photodetector to translate the light into a recordable signal to produce a profile of the gradient.

2. The apparatus as defined in claim 1, wherein the first and second light transmitting means are housed in the first probe needle.

3. The apparatus as defined in claim 2, wherein the first reflection means is also the second reflection means.

4. The apparatus as defined in claim 1, wherein the second light transmitting means is housed in a second needle that is simultaneously actuatable with the first needle.

5. The apparatus as defined in claim 1, wherein the first and second reflection means is a prism with a 45 degree reflecting angle.

6. The apparatus as defined in claim 4, wherein the first and second reflection means is a prism with a 45 degree reflecting angle.

7. The apparatus as defined in claim 1, additionally comprising means to prevent light of the excitation wavelength from receipt by the photodetector.

8. The apparatus as defined in claim 7, wherein said filter means is a bandpass filter.

* * * * *